US00PP10776P

United States Patent [19]

Wain

[11] Patent Number: Plant 10,776

[45] Date of Patent: Feb. 2, 1999

[54] CHRYSANTHEMUM PLANT NAMED 'FIRE TIME'

[75] Inventor: Peter Wain, Portsmouth, United Kingdom

[73] Assignee: Cleangro, Ltd., West Sussex, England

[21] Appl. No.: 838,353

[22] Filed: Apr. 8, 1997

[51] Int. Cl.[6] ..... A01H 5/00

[52] U.S. Cl. ..... Plt./78

[58] Field of Search ..... Plt./76, 78

*Primary Examiner*—Howard J. Locker
*Attorney, Agent, or Firm*—Christie, Parker & Hale, LLP

[57] ABSTRACT

A new and distinct cultivar of Chrysanthemum plant producing golden yellow flowers with an orange red center.

2 Drawing Sheets

BACKGROUND OF THE INVENTION

The present invention is directed to a new and distinct variety of Chrysanthemum botanically classified as *Dendranthema grandiflora*. The varietal denomination of the new chrysanthemum is 'Fire Time.'

The female and male parents of the new variety are undistributed, unpatented seedlings identified as P23-21 and P88- 19, respectivelly. The new variety has been asexually reproduced by vegetative cuttings in Ventura County, Calif. and the distinguishing characteristics are retained through successive generations of asexual reproduction.

SUMMARY OF THE INVENTION

'Fire Time' is a pot forcing chrysanthemum plant variety that can be grown as a disbud or spray type producing golden yellow flowers with an orange red center, and capable of being grown commercially in a greenhouse.

BRIEF DESCRIPTION OF ILLUSTRATIONS

The accompanying photographs show typical specimens of the new variety with colors being as nearly true as possible with illustrations of this type. One illustration shows 'Fire Time' grown as a pinched pot mum and the other illustration is a close-up of the flowers.

DESCRIPTION OF THE PLANT

The following description of the new variety is of specimens grown in a greenhouse in Ventura County, Calif. in the month of October. 'Fire Time' has not been observed under all possible environmental conditions. The phenotype may vary significantly with variations in the environment such as temperature, light intensity, day length and cultural conditions. Color values are taken from The Royal Horticultural Society Colour Chart.

Plants of the new variety have been grown successfully under temperature conditions averaging about 65° F. at night and about 75°–85° F. during the day under light conditions of about 5,000–6,000 foot candles. The plants respond well to use of growth retardant, such as one B9 treatment at about 2000 ppm. To produce a commercial product the plants may be pinched once and disbudded. It has been observed that the shelf life of 'Fire Time' is about 18 days with the response time of about 8 weeks.

Plant

Habit: Upright. Height: About 29.5 cm after one application of growth regulator as described.

Branching characteristics: Average to good.
Number of breaks from pinch: About 3 per.
Typical container size to be grown in: 4", 6", 8", 10".
Length of lateral branches:
*Average*.—About 24.4 cm.
Stem color: Near 139D.

Foliage

Leaf arrangement: Alternate.
Number of leaves per lateral branch:
*Average number leaves per lateral branch*.—About 15 fully mature leaves, very leafy.
(1) *Size*.—Length — Average about 8.75 cm; Width — Average about 5.1 cm.
(2) *Shape*.—Ovate.
(3) *Attachment*.—Petioled.
(4) *Apex*.—Acute.
(5) *Base*.—Truncate.

| (6) Color: | Mature | Young |
|---|---|---|
| Top: | Near 137A | Near 137B |
| Bottom: | Near 138B | Near 138B |

Margin: Lobed, denate.
Aspect: Generally flat, some slight undulation.
Surface characteristics:
*Top*.—Puberulent.
*Bottom*.—Puberulent. Venation: Palmately net; main veins prominent on underside of leaf; main vein coloration near 143D, veinlet coloration near 137D.
Petiole:
(1) *Length*.—About 2 cm.
(2) *Color*.—Near 144D.
Stipule: Very ocassionally 1 present, very small, about 0.2 cm across.

Flower

Inflorescence form: Cyme.
Flower form: Decorative.
Flower shape: Circular.
Flower color (general): Golden yellow with an orange red center near 34A caused by darker immature ray florets.
Blooms: Average about 5blooms per branch.
(1) *Diameter*.—Average about 8 cm.
(2) *Depth*.—Average about 5 cm.
(3) *Longevity on plant*.—About 18 day shelf life.
Sepal:
(1) *Number*. —About 30.

(2) *Color*.—Near 143C.
(3) *General appearance*.—Not very membraneous, thick and long on fully opened flowers.

Peduncle:
(1) *Length*.—Average about 5 cm.
(2) *Habit*.—Upright.
(3) *Surface*.—Tomentose.
(4) *Color*.—Near 144B.
(5) *Strength*.—Very stiff.

Bud:
(1) *Shape*.—Flattened sphere.
(2) *Diameter*.—Avg. about 0.9 cm.
(3) *Color*.—Near 143 C.
(4) *Height*.—About 0.5 cm.

Ray florets:
(1) *Number per flower*.—Average about 250.
(2) *Fused*.—No.
(3) *Texture*.—Smooth, matte.
(4) *Shape*.—Oblanceolate.
(5) *Apex*.—Obtuse with one notch.
(6) *Base*.—Tapered.
(7) *Margin*.—Entire.
(8) *Aspect*.—Strongly recurved, revolute at base.
(9) *Length*.—Avg. About 2.5 cm.
(10) *Avg.* —About 0.9 cm.
*Color—top side*.—Immature: Near 9A, some red streaks and speckles, near 42A. Mature: Near 7A. Fading: Near 8A.
*Color—under side*.—Immature: Near 12B, many red speckles. Mature: Near 9C. Fading: Near 8C.

Disc florets:
(1) *Number per flower*.—About 15.
(2) *Texture*.—Shiny, smooth.
(3) *Shape*.—Cylindric.
(4) *Margin*.—Entire.
(5) *Length*.—About 0.5 cm.
(6) *Width*.—About 0.1 cm.
(7) *Fragrance*.—Very light, musky.

Color:
*Immature*.—Near 59C.
*Mature*.—Near 59D.
*Fading*.—Near 65A.

Description of flower as it ages: Dark center disappears, flower becomes almost a sphere. Rayfloret tips brown and curl under.

Reproductive organs

Ray florets:
*Pistillate*.—(1) Pistil number: 1 per floret. (2) Ovary shape: Very flattened, wide sphere. (3) Stigma shape: Slightly curved out, very short. (4) Stigma color: Near 12A. (5) Style length: Average about 1 cm. (6) Style color: Near 154D .

Disc florets: Staminate and pistillate.

Pistillate:
(1) *Pistil number*.—1 per floret.
(2) *Stigma Shape*.—linear, near 7A.
(3) *Style Length*.—About 0.3 cm, clear.

Staminate:
(1) *Stamen number*.—About 6.
(2) *Anther length*.—About 0.2 cm.
(3) *Anther shape*.—linear, near 13A.
(4) *Pollen color*.—Near 13A.
(5) *Pollen quantity*.—Abundant.

What is claimed is:

1. A new and distinct variety of Chrysanthemum plant substantially as herein shown and described.

* * * * *

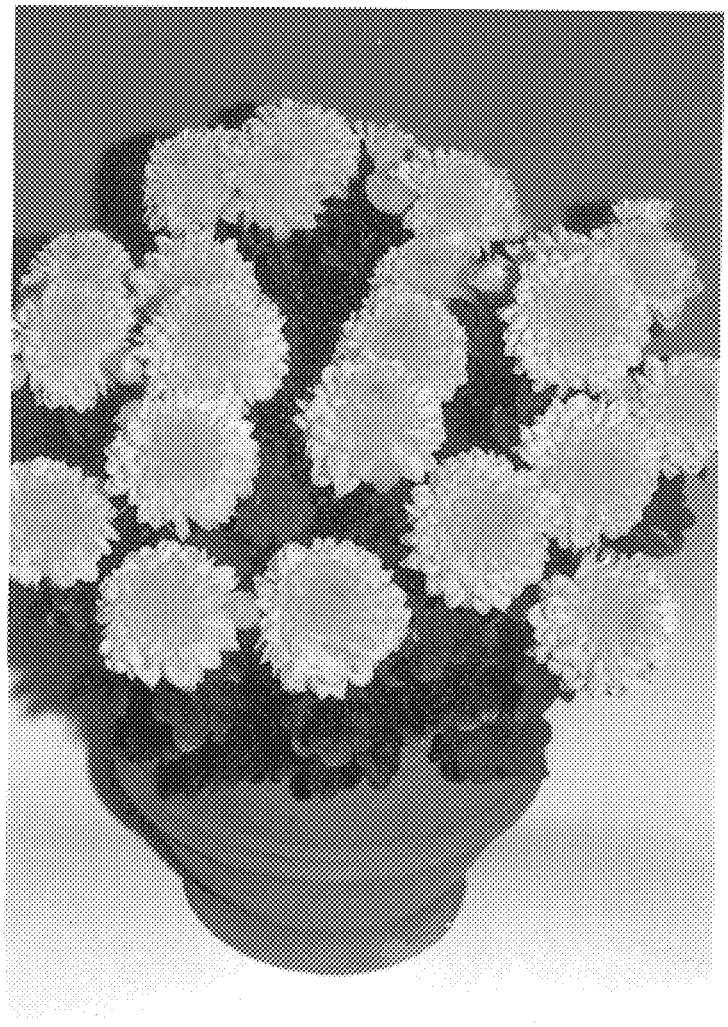

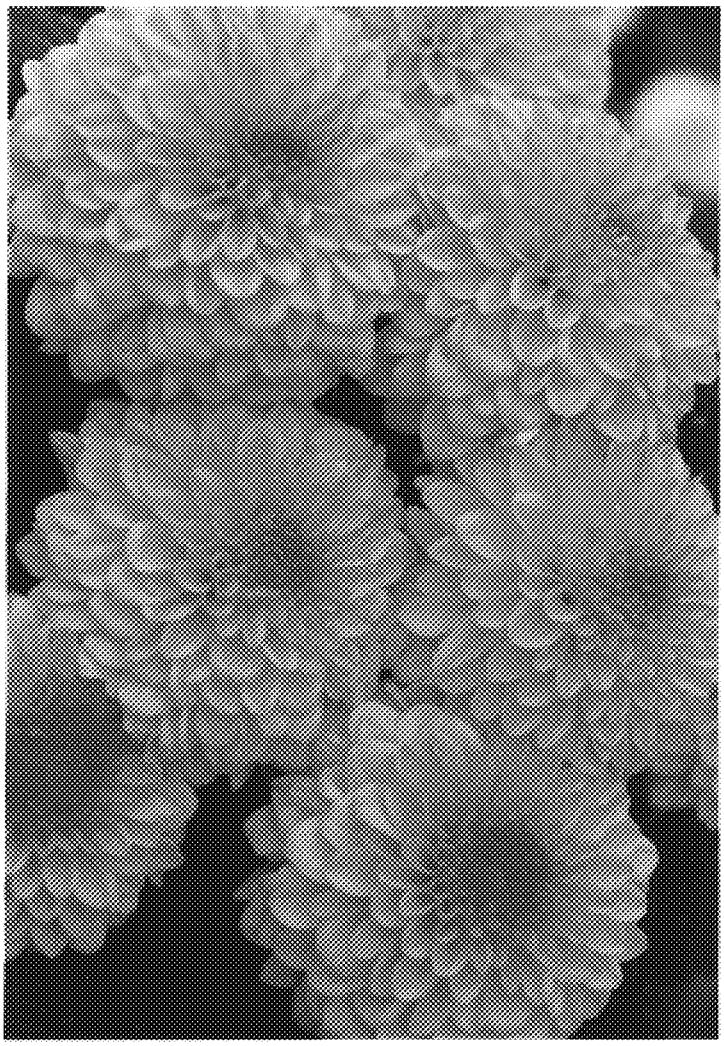

UNITED STATES PATENT AND TRADEMARK OFFICE

CERTIFICATE OF CORRECTION

PATENT NO. : PP 10,776
DATED : February 2, 1999
INVENTOR(S) : Peter Wain

It is certified that error appears in the above-identified patent and that said Letters Patent is hereby corrected as shown below:

Column 2,
Line 46, replace "5blooms" with -- 5 blooms --.

Column 3,
Line 25, the line should read -- (10) *Width* —Avg. About 0.9 cm. --.

Column 4,
Line 10, replace "Rayfloret" with -- Ray floret --.

Signed and Sealed this

Twentieth Day of November, 2001

*Attest:*

Nicholas P. Godici

NICHOLAS P. GODICI
*Acting Director of the United States Patent and Trademark Office*

*Attesting Officer*

UNITED STATES PATENT AND TRADEMARK OFFICE

CERTIFICATE OF CORRECTION

PATENT NO. : PP 10,776
DATED : February 2, 1999
INVENTORS) : Peter Wain

It is certified that error appears in the above-identified patent and that said Letters Patent is hereby corrected as shown below:

Column 2,
Line 46, replace "Sblooms" with -- 5 blooms --.

Column 3,
Line 25, the line should read -- *(10) Width -Avg.* About 0.9 cm. --.

Column 4,
Line 10, replace "Rayfloret" with -- Ray floret --.

Signed and Sealed this

Eighteenth Day of December, 2001

*Attest:*

*Attesting Officer*

JAMES E. ROGAN
*Director of the United States Patent and Trademark Office*